United States Patent [19]

Sawada et al.

[11] Patent Number: 4,956,123
[45] Date of Patent: Sep. 11, 1990

[54] METHOD FOR MANUFACTURE OF FLUORINE-CONTAINING AROMATIC DERIVATIVES

[75] Inventors: Hideo Sawada, Aichi; Michio Kobayashi; Masato Yoshida, both of Tokyo, all of Japan

[73] Assignee: Nippon Oils & Fats Company, Ltd., Tokyo, Japan

[21] Appl. No.: 246,017

[22] Filed: Sep. 14, 1988

Related U.S. Application Data

[63] Continuation of Ser. No. 818,811, Jan. 14, 1986, abandoned.

[30] Foreign Application Priority Data

Jan. 22, 1985 [JP] Japan .................................. 60-8459

[51] Int. Cl.$^5$ .......................... C07C 67/00; C07C 69/63
[52] U.S. Cl. .................................... 260/408; 560/138; 560/144; 560/227; 568/311; 568/335; 568/336; 568/645; 568/647; 568/649; 568/655; 568/928; 568/933; 568/936; 570/128; 570/142
[58] Field of Search .................. 560/227, 138, 144; 260/408

[56] References Cited

FOREIGN PATENT DOCUMENTS

| 693015 | 8/1964 | Canada ................................ 560/227 |
| 58-92627 | 6/1983 | Japan . |
| 58-92628 | 6/1983 | Japan . |
| 59-65042 | 4/1984 | Japan ................................ 560/227 |
| 60-123442 | 7/1985 | Japan ................................ 560/227 |
| 910599 | 3/1982 | U.S.S.R. ............................ 560/227 |

OTHER PUBLICATIONS

Weygand et al., Preparative Organic Chemistry, John Wiley & Sons, New York, 1972, pp. 396–399.
Journal of Organic Synthetic Chemical Society, vol. 44, No. 3

*Primary Examiner*—Vivian Garner
*Attorney, Agent, or Firm*—Oblon, Spivak, McClelland, Maier & Neustadt

[57] ABSTRACT

Fluorine-containing aromatic derivatives are produced by the reaction of di(haloacyl)peroxide represented by the general formula:

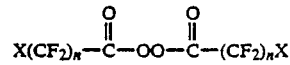

(wherein X stands for a fluorine, chlorine, or hydrogen atom and n for an integer of the value of 1 to 10) with aromatic unsaturated monomers represented by the general formula:

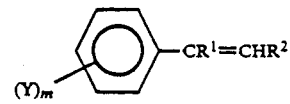

(wherein Y stands for hydrogen atom, methyl, ethyl, propyl, acetyl, propionyl, acetyloxy, propionyloxy, methoxy, ethoxy, propoxy, vinyl, isopropenyl, or nitro group, or a halogen atom, $R^1$ for hydrogen atom, methyl, ethyl, propyl, or butyl group, $R^2$ for hydrogen atom, methyl or phenyl group, and m for an integer of the value of 1 to 5).

13 Claims, No Drawings

METHOD FOR MANUFACTURE OF FLUORINE-CONTAINING AROMATIC DERIVATIVES

This application is a continuation of application Ser. No. 06/818,811, filed on 1/14/86.

FIELD OF THE INVENTION AND RELATED ART STATEMENT

This invention relates to a method for the manufacture of fluorine-containing aromatic derivatives, and more particularly to a method for more effective manufacture of fluorine-containing aromatic derivatives on a commercial scale.

Organic compounds containing perfluoroalkyl groups have come to attract growing attention owing to their useful properties such as the ability to manifest physiological activity. Further, organic compounds containing both unsaturated functional groups and perfluoroalkyl groups are useful as intermediates for the synthesis of agents for repelling water and oil, medicines, agricultural pesticides, and surface active agents and as monomers for the production of fluorine-containing polymers.

Heretofore, as means of incorporating a perfluoroalkyl group into an unsaturated functional group of an aromatic compound the cross-coupling reaction of an organic metal compound and a n organic halogenide has been know in the art. In the specifications of Japanese Patent Public Disclosures SHO 58(1983)-92627 and SHO 58(1983)-92628, for example, it is disclosed that 3-trifluoromethyl-3-phenyl-1-propene,

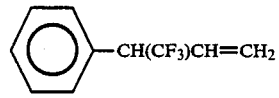

is obtained in a yield of 63% by causing zinc powder, trifluromethyl iodide, cinnamyl bromide, and palladium acetate to react in tetrahydrofuran by the action of ultrasonic waves.

Besides the crossing-coupling reaction by the use of such transition metal complexes as mentioned above, a method which effects the incorporation of a perfluroalkyl group into an unsaturated functional group of an aromatic compound by the use of an iodonium compound,

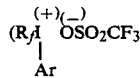

has been disclosed (Journal of Organic Synthetic Chemical Society, Vol. 41, No. 3, page 257 (1983)).

The conventional methods mentioned above, however, have posed the following problems.

The former method does not prove economically advantageous because the palladium catalyst is expensive and the reaction necessitates the action of ultrasonic waves. The iodonium salt method is economically disadvantageous because the iodonium salt is not easily synthesized and it is thermally unstable and the synthesis of the salt necessitates use of a special apparatus. Thus, there has existed no economically advantageous method which permits production of a fluorine-containing aromatic derivative by the incorporation of a perfluoroalkyl group into an unsaturated group of an aromatic unsaturated monomer. In the circumstances, the development of such a method has been desired.

OBJECT AND SUMMARY OF THE INVENTION

The object of this invention is to provide a fully industrially applicable method for manufacture of fluorine-containing aromatic derivative by incorporating a perfluoroalkyl group into an unsaturated group of an aromatic unsaturated monomer.

The inventors made a study in search of a method which is capable of producing the desired fluorine-containing aromatic derivatives in high yields. They have consequently found that fluorine-containing aromatic derivatives incorporating therein fluorine-containing aliphatic groups are obtained quickly and easily in high yields by the reaction of specific aliphatic di(haloacyl)-peroxides with specific aromatic unsaturated monomers. This invention has been perfected based on this knowledge.

To be specific, this invention is directed to the manufacture of fluorine-containing aromatic derivatives by the reaction of di(haloacyl)peroxides represented by the general formula (I):

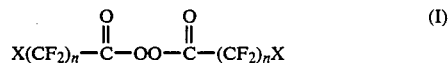

(wherein X stands for a fluorine, chlorine, or hydrogen atom and n for an integer of the value of 1 to 10) with aromatic unsaturated monomers represented by the general formula (II):

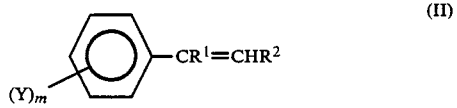

(wherein Y stands for hydrogen atom, methyl, ethyl, propyl, acetyl, propionyl, acetyloxy, propionyloxy, methoxy, ethoxy, propoxy, vinyl, isopropenyl, or nitro group, or a halogen atom, $R^1$ for hydrogen atom, methyl, ethyl, propyl, or butyl group, $R^2$ for hydrogen atom, methyl or phenyl group, and m for an integer of the value of 1 to 5). The fluorine-containing aromatic derivatives produced by the reaction mentioned above are as follows They are compounds represented by the general formula (III):

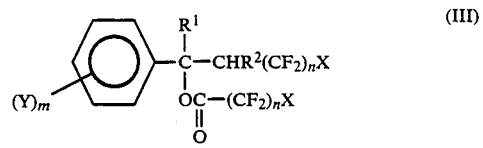

(wherein X and n have the same meanings as defined in general formula (I) and Y, m, $R^1$, and $R^2$ have the same meanings as defined in the general formula (II)) and compounds which have the aforementioned compounds as main components thereof and additionally contain therein compounds represented by the general formula (IV):

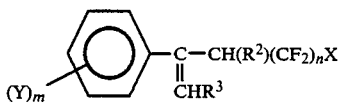

$$\text{(IV)}$$

(wherein $R^3$ stands for a hydrogen atom or a methyl, ethyl, or propyl group and X, Y, m, n, and $R^2$ have the same meanings as defined in the general formula (III)).

DESCRIPTION OF THE PREFERRED EMBODIMENTS

This invention is characterized by the use of di(haloacyl)peroxides represented by the aforementioned general formula (I). When aromatic unsaturated monomers are allowed to react with aliphatic diacyl peroxides such as, for example, octanoyl peroxide which are not substituted with fluorine, they are observed to undergo polymerization.

The value of the numeral represented by n in the aforementioned general formula (I) is limited to the range of 1 to 10 in consideration of the solubility of the di(haloacyl)peroxide in the reactive solvent, particularly a halogen aliphatic solvent. The value of n is not allowed to exceed 10 because the solubility of the di(haloacyl)peroxide is intolerably low if n exceeds 10.

Concrete examples of the di(haloacyl)peroxide represented by the general formula (I) and used effectively herein include bis(trifluoroacetyl)peroxide, bis(pentafluoropropionyl)peroxide, bis(heptafluorobutyryl)peroxide, bis(nonafluoropentanoyl)peroxide, bis(undecafluorohexanoyl)peroxide, bis(pentadecafluorooctanoyl)peroxide, bis(heptadecafluoropelargonyl)peroxide, bis(nonadecafluorodecanoyl)peroxide, bis(heneicosafluoroundecanoyl)peroxide, bis(4-chlorohexafluorobutyryl)peroxide, bis(4-H-hexafluorobutyryl)peroxide. Other examples of useful di(haloacyl)peroxide include bis(chlorodifluoroacetyl)peroxide, bis(3-chlorotetrafluoropropionyl)peroxide, bis(5-chlorooctafluoropentanoyl)peroxide, bis(6-chlorodecafluorohexanoyl)peroxide, bis(7-chlorododecafluoroheptanoyl)peroxide, bis(8-chlorotetradecafluorooctanoyl)peroxide, bis(9-chlorohexadecafluoropelargonyl)peroxide, bis(10-chlorooctadecaflorodecanoyl)peroxide, bis(11-chloroeicosafluoroundecanoyl)peroxide, bis(difluoroacetyl)peroxide, bis(3-H-tetrafluoropropionyl)peroxide, bis(6-H-decafluorohexanoyl)peroxide, bis(7-H-dodecafluoroheptanoyl)peroxide, bis(8-H-tetradecafluorooctanoyl)peroxide, bis(9-H-hexadecafluoropelargonyl)peroxide, bis(10-H-octadecafluorodecanoyl)peroxide, and bis(11-H-eicosafluoroundecanoyl)peroxide.

The di(haloacyl)peroxides represented by the aforementioned general formula (I) are desired to be diluted with a solvent during the course of production and handling. This solvent is desired to be a halogenated aliphatic solvent not containing any hydrogen atom.

Concrete examples of this solvent include 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, fluorotrichloromethane, hepta-fluoro-2,3,3-trichlorobutane, 1,1,1,3-tetrachlorotetrafluoropropane, 1,1,1-trichloropentafluoropropane, 1,1,1-trichlorotrifluoroethane, and 1,1,2-trichlorotrifluoroethane. For manufacture on a commercial scale, 1,1,2-trichlorotrifluoroethane proves particularly suitable among other halogenated aliphatic solvents enumerated above.

Concrete examples of the aromatic unsaturated monomer represented by the general formula (II) and used advantageously from the practical point of view include styrene, p-methylstyrene, p-ethylstyrene, p-propylstyrene, α-methylstyrene, 4-methyl-α-methylstyrene, 4-ethyl-α-methylstyrene, 4-propyl-α-methylstyrene,α-ethylstyrene, 4-methyl-αethylstyrene,α-butylstyrene, 4-methyl-α-butylstyrene, p-chlorostyrene, p-fluorostyrene, m-bromostyrene, 4-chloro-α-methylstyrene, 4-bromo-α-methylstyrene, 4-fluoro-α-methylstyrene,β-methylstyrene, 1,2diphenylethene, methyl-4-vinylphenyl ketone, 1-vinylphenyl acetate, methyl-4-vinylphenyl ether, 1,4-divinyl benzene, and 2,4-dimethyl styrene. Other examples of the monomer similarly useful effectively include 4-ethyl-α-ethylstyrene, 4-propyl-α-ethylstyrene, 4-ethyl-α-butylstyrene, 4-propyl-α-butylstyrene, p-bromostyrene, m-chlorostyrene, m-fluorostyrene, o-chlorostyrene, o-bromostyrene, o-fluorostyrene, 4-chloro-α-ethylstyrene, 4-bromo-α-ethylstyrene, 4-fluoro-α-ethylstyrene, 4-chloro-α-propylstyrene, 4-bromo-α-propylstyrene, 4-fluoro-α-propylstyrene, 4-chloro-α-butylstyrene, 4-bromo-α-butylstyrene, 4-methyl-β-methylstyrene, 4-ethyl-β-methylstyrene, 4-propyl-β-methylstyrene, 4-chloro-β-methylstyrene, 4-bromo-β-methylstyrene, 4-fluoro-β-methylstyrene, ethyl-4-vinylphenyl ketone, methyl-4-isopropenylphenyl ketone, ethyl-4-isopropenylphenyl ketone, 4-vinylphenyl propionate, 4-isopropenylphenyl acetate, 4-isopropenylphenyl propionate, ethyl-4-vinylphenyl ether, propyl-4-vinylphenyl ether, methyl-4-isopropenylphenyether, ethyl-4-isopropenylphenylether, propyl-4-isopropenylphenylether, 1,4-diisopropenyl benzene, 3-nitrostyrene, 3-nitro-α-methylstyrene, 3,4-dimethoxystyrene, 2,3,4,5,6-pentafluorostyrene, and 2,6-dichlorostyrene.

By this invention, a desired fluorine-containing aromatic derivative is produced. The principal component of the derivative so produced is a compound represented by the general formula (III). Depending on the reaction conditions, a compound represented by the general formula (IV) is simultaneously produced.

The condition for the formation of the fluorine-containing aromatic derivative of the general formula (IV) is that in the compound represented by the general formula (II),

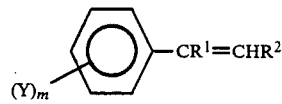

$$\text{(II)}$$

$R^1$ is a methyl, ethyl, propyl, or butyl group.

The ratios in which the compound represented by the general formula (III) and the compound represented by the general formula (IV) are formed in the reaction are about 75–90% and about 10–25%, respectively As already described, the di(haloacyl)peroxide is desired to be used in a form diluted in a solvent in the reaction. This dilution is desired to be such that the concentration of the di(haloacyl)peroxide in the solvent falls in the range of 2 to 20% by weight in order to assure safety during its production and handling The mixing ratio of the di(haloacyl)peroxide and the aromatic unsaturated monomer for the reaction is desired to be 1:1 to 10, preferably 1:1.5 to 5 by mol ratio.

If the mol ratio is less than 1, the yield in which the fluorine-containing aromatic derivative is produced tends to be impracticably low. If this mol ratio exceeds 10, the ratio of the unaltered aromatic unsaturated monomer remaining after the reaction tends to be impracticably high and the time required for isolation of the product to be impracticably long.

The reaction in this invention can be carried out under atmospheric pressure. The reaction temperature is generally in the range of 0° to 50° C., preferably 20° to 40° C. If the reaction temperature is less than 0° C., the time for the reaction tends to be impracticably long. Conversely if the reaction temperature is in excess of 50° C., the pressure of the reaction system during the reaction tends to become too high and the thermal polymerization of aromatic unsaturated monomer tends to proceed preferentially, making the operation of reaction difficult. The fluorine-containing aromatic derivative manufactured as described above can be identified in structure by gas chromatography, IR, and NMR.

The characteristics of the present invention are as follows.

(A) By the method of this invention, the fluorine-containing aromatic derivative represented by the general formula (III) or (IV) can be produced quickly and easily in a high yield by ready incorporation of the fluorine-containing aliphatic group into the unsaturated group of the aromatic unsaturated monomer. The reaction has no need for any reaction catalyst or for any special apparatus.

(B) From the fluorine-containing aromatic derivative represented by the general formula (III) and manufactured by the method of this invention, other fluorine-containing aromatic derivatives and fluorine-containing aromatic unsaturated monomers can be produced by the reaction shown below. For example, a fluorine-containing aromatic derivative possessing a hydroxyl group as represented by the following general formula (V) can be obtained by treating a compound represented by general formula (III) with an aqueous alkali solution.

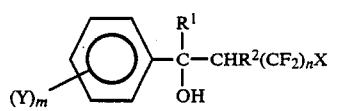
(V)

(wherein X, Y, n, m, $R^1$, and $R^2$ have the same meanings as defined in the general formula (III)).

The fluorine-containing aromatic derivatives possessing a hydroxyl group are highly useful as intermediates for the synthesis of various fluorine-containing aromatic derivatives because the aforementioned hydroxyl group is a reactive functional group.

Further, by treating the same compound with such acid as p-toluenesulfonic acid or sulfuric acid, a fluorine-containing aromatic unsaturated monomer represented by the general formula (VI):

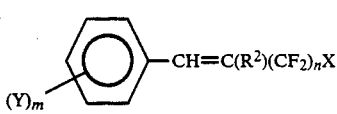
(VI)

(wherein X, Y, n, m, and $R^2$ have the same meanings as defined in the general formula (II)) or the general formula (IV):

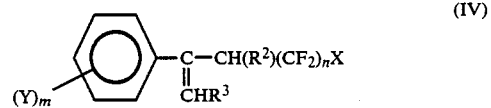
(IV)

(wherein $R^3$ stands for a hydrogen atom or a methyl, ethyl, or propyl group, and X, Y, n, m, and $R^2$ have the same meanings as defined in the general formula (III)) can be produced. Which of the compounds (VI) and (IV) is obtained by the treatment depends on the reaction conditions involved.

(C) Owing to the use of the fluorine-containing diacyl peroxide, the fluorine-containing aromatic derivative aimed at can be produced safely.

(D) The fluorine-containing aromatic derivatives produced by the present invention are useful as intermediates for the synthesis of agents for repelling water and oil, medicines, agricultural pesticides, and surface active agents and as monomers for the production of fluorine-containing polymers.

Now, the present invention will be described more specifically below with reference to working examples and referential experiments. The di(haloacyl)peroxides, aromatic monomer, fluorine-containing aromatic derivatives represented respectively by the general formulas (I), (II), (III), and (IV), and reaction conditions involved in the reactions of Examples 1–25 are shown collectively in Table 1, Table 2, and Table 3.

EXAMPLE 1

In a flask, a solution of 8.52 g (0.02 mol) of bis(heptafluorobutyryl)peroxide in 100 ml of 1,1,2-trichlorotrifluoroethane and 3.12 g (0.03 mol) of styrene subsequently added thereto were allowed to react at 30° C. for 5 hours under a flow of nitrogen. The reaction product so obtained was analyzed by gas chromatography, IR, and NMR. Consequently, the reaction was found to have produced 1-phenyl-2-heptafluoropropyl ethylheptafluorobutyrate

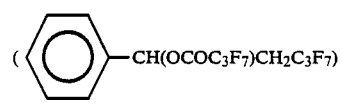

in a yield of 91%. The product and a boiling point of 73° to 74° C./5 mmHg.

REFERENTIAL EXPERIMENT 1

This experiment was carried out for the purpose of demonstrating that a compound of the general formula (V) and a compound of the general formula (VI) could be produced from the fluorine-containing aromatic derivative of Example 1.

Into 100 ml of 1,1,2-trichlorotrifluoroethane solution containing 4.86 g (0.01 mol) of 1-phenyl-2-heptafluoropropyl ethylheptafluorobutyrate

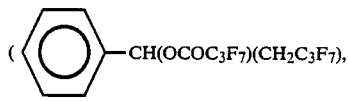

200 ml of an aqueous 10% sodium hydroxide solution was added and the obtained mixture was stirred. An organic layer was separated from the resultant mixture and the separated organic layer was dried with magnesium sulfate. By analysis of the reaction product, i.e. the separated and dried organic layer, by gas chromatography IR, and NMR, the reaction was found to have produced 1-hydroxy-1-phenyl-2-heptafluoropropyl ethane

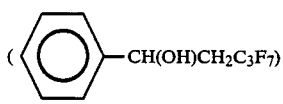

(corresponding to general formula) a yield of 99%.

Ten (10.0) ml of 1,1,2-trichlorotrifluoroethane containing 2.90 g (0.01 mol) of the above mentioned compound and 1 g of $p$-toluenesulfonic acid added thereto were refluxed at 50° C. for 10 hours. By analyzing the reaction product by gas chromatography, IR, and NMR, the reaction was found to have produced $\beta$-heptafluoropropylstyrene

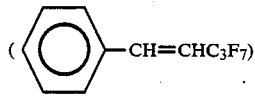

(corresponding to general formula VI) in yield of 97%.

EXAMPLE 2

In a flask, a solution of 8.52 g (0.02 mol) of bis(heptafluorobutyryl)peroxide in 100 ml of 1,1,2-trichlorotrifluoroethane and 3.55 g (0.03 mol) of α-methylstyrene subsequently added thereto were allowed to react at 40° C. for 3 hours under a flow of nitrogen. By analyzing the reaction product by gas chromatography, IR, and NMR, the reaction was found to have produced 2-phenyl-2-heptafluorobutyryloxy-1-heptafluoropropyl propane

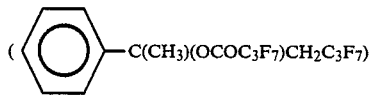

and
2-phenyl-1-heptafluoropropyl-2-propene

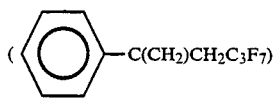

respectively in yields of 79% and 20%.

REFERENTIAL EXPERIMENT 2

In 100 ml of 1,1,2-trichlorotrifluoroethane solution containing 5.00 g (0.01 mol) of 2-phenyl-2-heptafluorobutyryloxy-1-heptafluoropropyl propane (⬡)—C(CH₃)(OCOC₃F₇)CH₂C₃F₇, 200 ml of an aqueous 10% sodium hydroxide solution added thereto was stirred. An organic layer was separated from the resultant mixture and was dried with magnesium sulfate. By analyzing the reaction product, i.e. the organic layer, by gas chromatography, IR, and NMR, the reaction was foundn to have produced 2-phenyl-2-hydroxy-1-heptafluoropropyl propane (⬡)—C(CH₃)(OH)CH₂C₃F₇)

in a yield of 98%.

When 100 ml of 1,1,2-trichlorotrifluoroethane solution containing 3.04 g (0.01 mol) of 2-phenyl-2-hydroxy-1-heptafluoropropane (⬡)—C(CH₃)(OH)CH₂C₃F₇)

and 5 g of $p$-toluenesulfonic acid added thereto were refluxed at 50° C. for 10 hours, there was obtained 2-phenyl-1-heptafluoropropyl-2-propane (⬡)—C(CH₂)CH₂C₃F₇)

in a yield of 96%.

EXAMPLES 3–24

Fluorine-containing aromatic derivatives represented by the general formulas (III) and (IV) were produced by following the procedure of Example 1, except that the di(haloacyl)peroxide represented by the general formula (I) and the aromatic unsaturated monomer represented by the general formula (II) were varied in kind and the mol ratio and the reaction conditions were also varied. The specific compounds of the general formulas (I), (II), (III), and (IV), the reaction conditions, the mol ratios of (I) to (II), and the yields of (III) and (IV) mentioned above are shown in Table 1, Table 2, and Table 3.

TABLE 1

| Example | | 1 | 2 | 3 | 4 | 5 | 6 | 7 | 8 | 9 | 10 |
|---|---|---|---|---|---|---|---|---|---|---|---|
| (I) Di(haloacyl)peroxide | X | F | F | F | F | H | Cl | F | F | F | F |

TABLE 1-continued

| Example | | 1 | 2 | 3 | 4 | 5 | 6 | 7 | 8 | 9 | 10 |
|---|---|---|---|---|---|---|---|---|---|---|---|
| (X(CF$_2$)$_n$C(=O)—O)$_2$ | n | 3 | 3 | 7 | 1 | 3 | 3 | 3 | 3 | 3 | 3 |
| | Amount (g) | 8.52 | 8.52 | 16.52 | 4.52 | 7.78 | 9.18 | 8.52 | 8.52 | 8.52 | 8.52 |
| | Mol | 0.02 | 0.02 | 0.02 | 0.02 | 0.02 | 0.02 | 0.02 | 0.02 | 0.02 | 0.02 |
| (II) Aromatic unsaturated monomer | Y | H | H | H | H | H | H | p-CH$_3$ | p-Cl | m-Br | p-F |
| (Y)$_m$—C$_6$H$_4$—CR$^1$=CHR$^2$ (m = 1) | R$^1$ | H | CH$_3$ | H | H | H | H | H | H | H | H |
| | R$^2$ | H | H | H | H | H | H | H | H | H | H |
| | Amount (g) | 3.12 | 3.55 | 3.12 | 3.12 | 4.17 | 3.12 | 3.55 | 8.70 | 5.49 | 3.66 |
| | Mol | 0.03 | 0.03 | 0.03 | 0.03 | 0.04 | 0.03 | 0.03 | 0.05 | 0.03 | 0.03 |
| Mol ratio of (I) to (II) | | 1:1.5 | 1:1.5 | 1:1.5 | 1:1.5 | 1:2.0 | 1:1.5 | 1:1.5 | 1:2.5 | 1:1.5 | 1:1.5 |
| Reaction conditions | Temperature(°C.) | 30 | 40 | 30 | 30 | 30 | 30 | 30 | 40 | 35 | 30 |
| | Time (hour) | 5 | 3 | 6 | 5 | 7 | 8 | 10 | 10 | 15 | 17 |
| Fluorine-containing aromatic derivative (III) | R$^1$ | H | CH$_3$ | H | H | H | H | H | H | H | H |
| | R$^2$ | H | H | H | H | H | H | H | H | H | H |
| (Y)$_m$—C$_6$H$_4$—C(R$^1$)(OC(=O)(CF$_2$)$_n$X)—CH(CF$_2$)$_n$X (m = 1) | Y | H | H | H | H | H | H | p-CH$_3$ | p-Cl | m-Br | p-F |
| | X | F | F | F | F | H | Cl | F | F | F | F |
| | n | 3 | 3 | 7 | 1 | 3 | 3 | 3 | 3 | 3 | 3 |
| | Yield (%) | 91 | 79 | 86 | 83 | 88 | 94 | 96 | 89 | 85 | 79 |
| (IV) | R$^2$ | — | H | — | — | — | — | — | — | — | — |
| (Y)$_m$—C$_6$H$_4$—C(CHR$^3$)(=O?)—CH(R$^2$)(CF$_2$)$_n$X | R$^3$ | — | H | — | — | — | — | — | — | — | — |
| | Y | — | H | — | — | — | — | — | — | — | — |
| | X | — | F | — | — | — | — | — | — | — | — |
| | n | — | 3 | — | — | — | — | — | — | — | — |
| | Yield (%) | — | 20 | — | — | — | — | — | — | — | — |

TABLE 2

| Example | | 11 | 12 | 13 | 14 | 15 | 16 | 17 | 18 | 19 | 20 |
|---|---|---|---|---|---|---|---|---|---|---|---|
| (I) Di(haloacyl)peroxide | X | F | F | H | Cl | F | F | F | F | F | F |
| (X(CF$_2$)$_n$C(=O)—O)$_2$ | n | 7 | 1 | 3 | 3 | 3 | 3 | 3 | 3 | 3 | 3 |
| | Amount (g) | 16.52 | 4.52 | 7.78 | 9.18 | 8.52 | 8.52 | 8.52 | 8.52 | 8.52 | 8.52 |
| | Mol | 0.02 | 0.02 | 0.02 | 0.02 | 0.02 | 0.02 | 0.02 | 0.02 | 0.02 | 0.02 |
| (II) Aromatic unsaturated monomer | Y | H | H | H | H | 4-CH$_3$ | 4-Cl | 4-Br | 4-F | H | H |
| (Y)$_m$—C$_6$H$_4$—CR$^1$=CHR$^2$ (m = 1) | R$^1$ | CH$_3$ | CH$_3$ | CH$_3$ | CH$_3$ | CH$_3$ | CH$_3$ | CH$_3$ | CH$_3$ | H | H |
| | R$^2$ | H | H | H | H | H | H | H | H | CH$_3$ | C$_6$H$_5$ |
| | Amount (g) | 3.55 | 3.55 | 7.09 | 3.55 | 3.97 | 4.58 | 5.91 | 4.09 | 3.55 | 5.41 |
| | Mol | 0.03 | 0.03 | 0.06 | 0.03 | 0.03 | 0.03 | 0.03 | 0.03 | 0.03 | 0.03 |
| Mol ratio of (I) to (II) | | 1:1.5 | 1:1.5 | 1:3.0 | 1:1.5 | 1:1.5 | 1:1.5 | 1:1.5 | 1:1.5 | 1:1.5 | 1:1.5 |
| Reaction conditions | Temperature(°C.) | 40 | 20 | 25 | 30 | 30 | 40 | 40 | 40 | 40 | 40 |
| | Time (hour) | 5 | 15 | 10 | 6 | 5 | 6 | 15 | 12 | 10 | 6 |
| Fluorine-containing aromatic derivative (III) | R$^1$ | CH$_3$ | CH$_3$ | CH$_3$ | CH$_3$ | CH$_3$ | CH$_3$ | CH$_3$ | CH$_3$ | H | H |
| | R$^2$ | H | H | H | H | H | H | H | H | CH$_3$ | C$_6$H$_5$ |
| (Y)$_m$—C$_6$H$_4$—C(R$^1$)(OC(=O)(CF$_2$)$_n$X)—CH(CF$_2$)$_n$X (m = 1) | Y | H | H | H | H | 4-CH$_3$ | 4-Cl | 4-Br | 4-F | H | H |
| | X | F | F | H | Cl | F | F | F | F | F | F |
| | n | 7 | 1 | 3 | 3 | 3 | 3 | 3 | 3 | 3 | 3 |
| | Yield (%) | 81 | 85 | 76 | 80 | 87 | 73 | 76 | 71 | 75 | 81 |
| (IV) | R$^2$ | H | H | H | H | H | H | H | H | — | (a) |

TABLE 2-continued

| Example | | 11 | 12 | 13 | 14 | 15 | 16 | 17 | 18 | 19 | 20 |
|---|---|---|---|---|---|---|---|---|---|---|---|
| 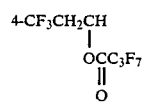 (Y)$_m$ (m = 1) —C(=CHR$^3$)—CH(R$^2$)(CF$_2$)$_n$X | R$^3$ | H | H | H | H | H | H | H | H | — | |
| | Y | H | H | H | H | 4-CH$_3$ | 4-Cl | 4-Br | 4-F | — | |
| | X | F | F | H | Cl | F | F | F | F | — | |
| | n | 7 | 1 | 3 | 3 | 3 | 3 | 3 | 3 | — | |
| | Yield (%) | 12 | 9 | 15 | 11 | 10 | 20 | 15 | 22 | — | 12 |

(a) product C$_6$H$_5$—CH=C(C$_3$F$_7$)C$_6$H$_5$

TABLE 3

| Example | | 21 | 22 | 23 | 24 |
|---|---|---|---|---|---|
| (I) Di(haloacyl)peroxide $$(X(CF_2)_n\overset{O}{\underset{\|}{C}}-O)_2$$ | X | F | F | F | F |
| | n | 3 | 3 | 3 | 3 |
| | Amount (g) | 8.52 | 8.52 | 17.04 | 8.52 |
| | Mol | 0.02 | 0.02 | 0.04 | 0.02 |
| (II) Aromatic unsaturated monomer | Y | m = 2 2,4-dimethyl | m = 1 4-CH$_3$O | m = 1 4-CH$_2$=CH | (b) |
| —CR$^1$=CHR$^2$ (m = 1~5) | R$^1$ | H | H | H | H |
| | R$^2$ | H | H | H | H |
| | Amount (g) | 3.97 | 4.03 | 3.91 | 5.82 |
| | Mol | 0.03 | 0.03 | 0.03 | 0.03 |
| Mol ratio of (I) to (II) | | 1:1.5 | 1:1.5 | 1:0.75 | 1:1.5 |
| Reaction conditions | Temperature(°C.) | 30 | 30 | 30 | 40 |
| | Time (hour) | 15 | 15 | 20 | 20 |
| Fluorine-containing aromatic derivative (III) | R$^1$ | H | H | H | H |
| | R$^2$ | H | H | H | H |
| | Y | m = 2 2,4-dimethyl | m = 1 4-CH$_3$O | (a) | (b) |
| —C(—CH(CF$_2$)$_n$X)(OC(=O)(CF$_2$)$_n$X) | X | F | F | F | F |
| | n | 3 | 3 | 3 | 3 |
| | Yield (%) | 89 | 82 | 75 | 49 |
| (IV) | R$^2$ | — | — | — | — |
| | R$^3$ | — | — | — | — |
| | Y | — | — | — | — |
| —C(=CHR$^3$)—CH(R$^2$)(CF$_2$)$_n$X | X | — | — | — | — |
| | n | — | — | — | — |
| | Yield (%) | — | — | — | — |

(a) m = 1
4-CF$_3$CH$_2$CH(OCC$_3$F$_7$)
           ‖
           O (b) m = 5  2,3,4,5,6-pentafluoro

What is claimed is:

1. A method for the manufacture of a fluorine-containing aromatic compound having the formula (III):

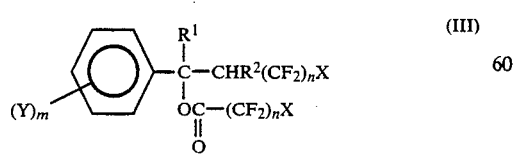

wherein X is selected from the group consisting of fluorine, chlorine and hydrogen, Y is selected from the group consisting of hydrogen, methyl, ethyl, propyl, acetyl, propionyl, acetyloxy, propionyloxy, methoxy, ethoxy, propoxy, vinyl, isopropenyl, nitro, and halogen; R$^1$ is selected from the group consisting of hydrogen, methyl, ethyl, propyl and butyl; R$^2$ is selected from the group consisting of hydrogen, methyl and phenyl; n is an integer of 1–10; and m is an integer of 1–5; which comprises reacting at a temperature of about 0°–50° C., a di(haloacyl)peroxide having the formula (I):

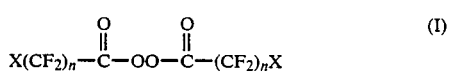

wherein X and n are as defined above in the formula (III) with an aromatic unsaturated monomer having the formula (II):

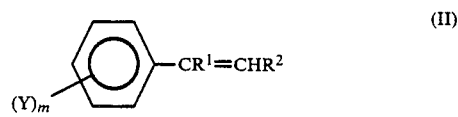

wherein Y, $R^1$, $R^2$ and m are as defined in the formula (III).

2. The method according to claim 1, wherein said di(haloacyl)peroxide is selected from the group consisting of bis(trifluoroacetyl)peroxide, bis(pentafluoropropionyl)peroxide, bis(heptafluorobutyryl)-peroxide, bis(nonafluoropentanoyl)peroxide, bis(undecafluorohexanoyl)peroxide, bis(pentadecafluoro-octanoyl)peroxide, bis(heptadecafluoropelargonyl)peroxide, bis(nonadecafluorodecanoyl)peroxide, bis(heneicosafluoroundecanoyl)peroxide, bis(4-chlorohexafluorobutyryl)-peroxide, and bis(4-H-heaxafluorobutyryl)peroxide.

3. The method according to claim 1, wherein said aromatic monomer is selected from the group consisting of styrene, $p$-methylstryene, $p$-ethylstyrene, $p$-propylstyrene, $\alpha$-methylstyrene, 4-methyl-$\alpha$-methyl-styrene, 4-ethyl-$\alpha$-methylstyrene, 4-propyl-$\alpha$-methylstyrene, $\alpha$-ethylstyrene, 4-methyl-$\alpha$-ethylstyrene, $\alpha$-butylstyrene, 4-methyl-$\alpha$-butylstyrene, $p$-chlorostyrene, $p$-fluorostyrene, m-bromostyrene, 4-chloro-$\alpha$-methylstyrene, 4-bromo-$\alpha$-methylstyrene, 4-fluoro-$\alpha$-methylstyrene, $p$- methylstyrene, 1,2-diphenylethane, methyl-4-vinylphenyl ketone, 4-vinylphenyl acetate, methyl-4-vinylphenyl ether, 1,4-divinyl benzene, and 2,4-dimethylstyrene.

4. The method according to claim 1, wherein said di(haloacyl)peroxide is selected from the group consisting of bis(chlorodifluoroacetyl)peroxide, bis( 3-chlorotetrafluoropropionyl)peroxide, bis(5-clorooctafluoropentanoyl)peroxide, bis(6-chlorodecafluorohexanoyl)peroxide, bis(7-chlorododecafluoroheptanoyl)-peroxide, bis(8-chlorotetradecafluorooctanoyl)peroxide, bis(9-chlorohexadecafluoropelargonyl)peroxide, bis(10-clorooctaddecafluorodecanoyl)peroxide, bis(11-chloroeicosafluoroundecanoyl)peroxide, bis(difluoroacetyl)peroxide, bis(3-H-tetrafluoropropionyl)-peroxide, bis(6-H-decafluorohexanoyl)peroxide, bis(7-H-dodecafluoroheptanoyl)peroxide, bis(8-H-tetradecafluorooctanoyl)peroxide, bis(9-H-hexadecafluoropelargonyl)peroxide, bis(10-H-octadecafluorodecanoyl)peroxide, and bis(11-H-eicosafluoroundecanoyl)peroxide.

5. The method according to claim 1, wherein said reaction is effected at a temperature in the range of 20° to 40° C.

6. The method according to claim 1, wherein said di(haloacyl)peroxide and said aromatic unsaturated monomer are used in a mol ratio of 1:1 to 10 for said reaction.

7. The method according to claim 6, wherein said di(haloacyl)peroxide and said aromatic unsaturated monomer are used in a molar ratio of 1:1.5 to 5 for said reaction.

8. The method according to claim 1, wherein said di(haloacyl)peroxide is used in said reaction in a form diluted with a solvent.

9. The method according to claim 8, wherein said di(haloacyl)peroxide is used in said solvent at a concentration in the range of 2 to 20% by weight.

10. The method of claim 8, wherein said solvent is a halogenated aliphatic solvent containing no hydrogen atom.

11. The method according to claim 10, wherein said solvent is selected from the group consisting of 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetracloroethane, fluorotrichloromethane, hepta-fluoro-2,3,3-trichlorobutane, 1,1,1,3-tetrachlorotetrafluoropropane, 1,1,1-trichloropentafluoropropane, 1,1,1-trichlorotrifluoroethane, and 1,I,2-trichlorotrifluoroethane.

12. The method according to claim 11, wherein said solvent is 1,1,2-trichlorotrifluoroethane.

13. The method according to claim 10, wherein said monomer is selected from the group consisting of 4-ethyl-$\alpha$-ethylstyrene, 4-propyl-$\alpha$ethylstyrene, 4-ethyl-$\alpha$-butylstyrene, 4-propyl-$\alpha$butylstyrene, $p$-bromostyrene, m-chlorostyrene, m-fluorostyrene, o-chlorostyrene, o-bromostyrene, o-fluorostyrene, 4-chloro-$\alpha$-ethylstyrene, 4-bromo-$\alpha$-ethylstyrene, 4-fluoro-$\alpha$-ethylstyrene, 4-chloro-$\alpha$-propylstyrene, 4-bromo-$\alpha$-propylstyrene, 4-fluoro-$\alpha$-propyl styrene, 4-chloro-$\alpha$-butylstyrene, 4-bromo--butylstyrene, 4-methyl-$\beta$-methylstyrene, 4-ethyl-$\beta$-methyl-styrene, 4-propyl-$\beta$-methyl styrene, 4-chloro-$\beta$-methylstyrene, 4-bromo-$\beta$-methylstyrene, 4-fluoro-$\beta$-methylstyrene, ethyl-4-vinylphenyl ketone, methyl-4-isopropenylphenyl ketone, ethyl-4-isopropenylphenyl ketone, 4-vinylphenyl propionate, 4-isopropenylphenyl acetate, 4-isopropenylphenylpropionate, ethyl-4-vinylphenyl ether, propyl-4-vinylphenylether, methyl-4-isopropenylphenylether, ethyl-4-isopropenylphenylether, propyl-4-isoproxenylphenylether,1,4-diisopropenyl benzene, 3-nitrostyrene, 3-nitro-$\alpha$-methylstyrene, 3,4-dimethoxystyrene, 2,3,4,5,6-pentafluorostyrene and 2,6-dichlorostyrene.

* * * * *